(12) United States Patent
Combes et al.

(10) Patent No.: US 11,318,255 B2
(45) Date of Patent: May 3, 2022

(54) SYRINGE WITH LOCKING MECHANISM

(71) Applicant: SOFIC (STÉ FRANAISE D'INSTRUMENTS DE CHIRURGIE), Mazamet (FR)

(72) Inventors: Christophe Combes, Mazamet (FR); Richard Foulon, Aussillon (FR)

(73) Assignee: SOFIC (STÉ FRANCAISE D'INSTRUMENTS DE CHIRURGIE), Mazamet (FR)

( * ) Notice: Subject to any disclaimer, the term of this patent is extended or adjusted under 35 U.S.C. 154(b) by 39 days.

(21) Appl. No.: 16/643,960

(22) PCT Filed: Sep. 12, 2018

(86) PCT No.: PCT/EP2018/074629
§ 371 (c)(1),
(2) Date: Mar. 3, 2020

(87) PCT Pub. No.: WO2019/053072
PCT Pub. Date: Mar. 21, 2019

(65) Prior Publication Data
US 2020/0405963 A1 Dec. 31, 2020

(30) Foreign Application Priority Data
Sep. 12, 2017 (EP) .................................... 17306173

(51) Int. Cl.
*A61M 5/315* (2006.01)
*A61M 5/24* (2006.01)
*A61M 5/31* (2006.01)

(52) U.S. Cl.
CPC .......... *A61M 5/31501* (2013.01); *A61M 5/24* (2013.01); *A61M 5/3137* (2013.01); *A61M 5/31513* (2013.01); A61M 2005/2403 (2013.01)

(58) Field of Classification Search
CPC .... A61M 2005/247; A61M 2005/3247; A61M 5/24; A61M 5/315; A61M 5/31501; A61M 5/3243; A61M 5/3257
See application file for complete search history.

(56) References Cited

U.S. PATENT DOCUMENTS

| 4,834,717 A * | 5/1989 | Haber ..................... A61M 5/24 604/193 |
| 5,242,416 A | 9/1993 | Hutson |
| 6,776,775 B1 | 8/2004 | Mohammad |

FOREIGN PATENT DOCUMENTS

| FR | 2633520 A1 | 1/1990 |
| FR | 2 958 548 A1 | 10/2011 |

(Continued)

OTHER PUBLICATIONS

International Search Report dated Nov. 6, 2018 in corresponding International application No. PCT/EP2018/074629; 10 pages including Machine-generated English-language translation.

*Primary Examiner* — Deanna K Hall
(74) *Attorney, Agent, or Firm* — Maier & Maier, PLLC

(57) ABSTRACT

A syringe including an injection syringe body and a syringe handle, configured to cooperate with one another in order to ensure a locking function between the injection syringe body and the syringe handle. The injection syringe body includes a longitudinal hub including at least one female or male retaining element, and a protective sheath moveable along said longitudinal hub and able to cover in a retracted position the at least one retaining element of the longitudinal hub. The syringe handle includes at least one male or female retaining element intended to cooperate with the at least one female or male retaining element of the longitudinal hub, ensuring a retaining function, the cooperation being named locking position. The syringe further includes at least one blocker, the at least one blocker ensuring a radial holding (Continued)

function when the retracted and the locking positions are both engaged.

17 Claims, 7 Drawing Sheets

(56) References Cited

FOREIGN PATENT DOCUMENTS

| GB | 741 604 A | 12/1955 | | |
|---|---|---|---|---|
| WO | 90/00073 A | 1/1990 | | |
| WO | 2014/184321 A2 | 11/2014 | | |
| WO | WO-2014184321 A2 * | 11/2014 | .......... | A61M 5/3257 |

* cited by examiner

SYRINGE WITH LOCKING MECHANISM

FIELD

The present invention pertains to the field of syringes and especially to the field of dentistry. In particular, the invention relates to a system for locking an injection syringe body relative to a syringe handle.

BACKGROUND

An injection syringe system comprises two mains parts: a syringe handle configured to be handled by a technician, and a body configured to comprise a needle and a compartment for stocking the liquid to be injected or sampled.

The invention relates to a syringe of the type having an injection needle for single use, notably for dentistry.

The classic syringes used in dentistry have a handle provided with a plunger and finger grip ribs and a syringe body able to be screwed removably onto this handle after a cartridge has been put in place. This body further has a threaded nose for the screwing of a base carrying a needle, initially packaged in a protective case so as to avoid any risk of pricking when handling this needle and when screwing the base onto the syringe body. The protective case having been removed for use of the syringe is then put back in place for the unscrewing of the base. This type of syringe has four major disadvantages. Firstly, when the needle is capped again, the protective case will be opposite the end of the needle and accidents of pricking are relatively frequent with all the risks that pricking with a dirty needle involves. Furthermore, the syringe body intended to be reused is soiled by the patient's saliva, necessitating complete sterilization of this body after use. Besides, the cartridge is not protected during oral injection, despite the risks of accidental bursting thereof, due to the high pressures necessary for the injection of the liquid. Lastly, the operations of screwing and unscrewing, on the one hand of the base on the syringe body, and on the other hand, of the syringe body on the handle, are operations that are relatively long for the practitioner.

It also known from French patent application FR2633520 a single use syringe comprising a reusable handle. The locking system between the syringe and the handle comprises an annular notch at the longitudinal opened end of the syringe configured to cooperate with a rib of the sleeve of the handle when the sleeve is lodged inside the longitudinal opened end of the syringe. The syringe further comprises a moveable protective sheath able to shield the needle in one position and to cover the locking system in another position.

This type of syringe is made of plastic material such as polypropylene. Indeed, polypropylene is not expensive, easy to manufacture, compatible with the medical needs, and present some elasticity which enables the material to be deformed in such a way as to allow the rib to enter into the annular notch.

A drawback of this system is that the elasticity of the polypropylene can cause a disengagement between the handle and the syringe. Indeed, especially in the dentistry field, the interface between the handle and the syringe is often subjected to strains transversal to the longitudinal axis of the syringe. The elasticity of the plastic material coupled to said transversal force may strain the syringe enough to cause the disengagement of the handle from the syringe during use.

Therefore, there is a need for a syringe body and a reusable handle comprising a safe locking system, quick and easy to mount, strongly reducing risks of pricking with the needle before and after use, and cost effective.

SUMMARY

The present invention relates to a syringe comprising an injection syringe body and a syringe handle, configured to cooperate with one another in order to ensure a locking function between the injection syringe body and the syringe handle. The injection syringe body comprises a longitudinal hub comprising at least one female or male retaining means, and a protective sheath moveable along said longitudinal hub and able to cover in a retracted position the at least one retaining means of the longitudinal hub. The syringe handle comprises at least one male or female retaining means intended to cooperate with the at least one female or male retaining means of the longitudinal hub, ensuring a retaining function, said cooperation being named locking position. The syringe further comprises at least one blocker, said at least one blocker ensuring a radial holding function when the retracted and the locking positions are both engaged.

According to one embodiment, each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide. In this way, risks of unintentional withdrawal of the male means from the female retaining means are avoided. In particular, the anti-return means make the displacement of a male retaining means from the female retaining means toward the slide more difficult than its displacement from the slide into the female retaining means.

According to one embodiment where the longitudinal hub comprises at least one female retaining means and the syringe handle comprises at least one male retaining means intended to cooperate with the at least one female retaining means of the longitudinal hub, the longitudinal hub further comprises an inlet and a slide adapted to guide the at least one male means of the syringe handle from the inlet into the female means.

According to one embodiment, the anti-return means comprise a width of the slide which is narrower than the length of the male retaining means according to a longitudinal direction of the longitudinal hub.

According to one embodiment, the width of the slide is narrower than the width of the female retaining means.

According to one embodiment, the Young's modulus of the part comprising the female retaining means is lower than the Young's modulus of the male retaining means or the part comprising the male means.

In particular, in the case where the syringe handle comprises at least one male means protruding from its outer surface and the longitudinal hub comprises at least one female means configured to house the male retaining means of the syringe handle, the Young's modulus of the longitudinal hub is advantageously lower than the Young's modulus of the male retaining means, so that the longitudinal hub is deformed during the sliding and not the male retaining means.

In the case where the longitudinal hub comprises at least one male means protruding from its inner surface and the syringe handle comprises at least one female means configured to house the male retaining means of the longitudinal hub, the Young's modulus of the male retaining means of the longitudinal hub is higher than the Young's modulus of the syringe handle, so that the syringe handle is deformed during the sliding and not the male retaining means.

According to one embodiment, the anti-return means comprise a step in the direction of the translation of the male retaining means out of the female means toward the slide.

According to one embodiment, the slide comprises at least two portions forming an angle at the boundary between the two portions.

According to one embodiment, the slide has an L-shape.

According to one embodiment, the slide comprises at least one through slot between the boundary between the two portions of the slide and the female retaining means.

According to one embodiment, the at least one blocker ensures the radial holding function by at least partially covering the protective sheath.

According to one embodiment, the syringe handle comprises the at least one blocker.

According to one embodiment, the syringe comprises at least two blockers and, when the retracted and the locking positions are both engaged, the at least two blockers are regularly positioned around the protective sheath.

According to one embodiment, at least one retaining means of the longitudinal hub is located in the vicinity of a first longitudinal end of the hub and the injection syringe body further comprises a needle fitted with a second end of the longitudinal hub opposite from said first end, said needle comprising an external portion extending outside said longitudinal hub.

According to one embodiment, the protective sheath is moveable along said longitudinal hub between at least two positions:
   an extended position, where the external portion of the needle is inside the protection sheath; and
   the retracted position where at least a part of the external portion of the needle is extended outside the protective sheath and said protective sheath covers the at least one retaining means.

According to one embodiment, the longitudinal hub further comprises a compartment between the first end and the second end of said hub, configured to receive a cartridge.

According to one embodiment, the needle further comprises an internal portion extending inside said compartment of the longitudinal hub.

According to one embodiment, the inner diameter of the protective sheath is substantially equal to the outer diameter of the longitudinal hub.

According to one embodiment, the at least one blocker is curved and the radius of curvature of the inner surface of the at least one blocker is substantially equal to the radius of curvature of the outer surface of the protective sheath.

The present invention also relates to a syringe handle adapted to cooperate with an injection syringe body according to the present invention comprising at least one female or male retaining means and at least one protective sheath moveable along a longitudinal hub of the injection syringe body, said syringe handle comprising:
   at least one male or female retaining means intended to cooperate with at least one female or male retaining means of the injection syringe body, ensuring a retaining function, said cooperation being named locking position; and
   at least one blocker adapted to cooperate with a protective sheath of the injection syringe body in a predefined position, the at least one blocker ensuring a radial holding function when the predefined position of the protective sheath and the locking position are both engaged.

According to one embodiment, each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide.

The present invention also relates to an injection syringe body adapted to cooperate with a syringe handle according to the present invention comprising at least one male or female retaining means, said injection syringe body comprising:
   a longitudinal hub comprising at least one female or male retaining means configured to maintain longitudinally a male or female retaining means of a syringe handle;
   a protective sheath moveable along said longitudinal hub and able to cover in a retracted position the at least one female or male retaining means of the longitudinal hub, wherein the cooperation between the injection syringe body and a syringe handle is locked when the retracted position is activated.

According to one embodiment, each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide.

Definitions

In the present invention, the following terms have the following meanings:
   "Groove" refers to an elongated blind hole, e.g. cut into a flat plate or into the surface of a cylinder.
   "Inner" refers to a location closer to the longitudinal axis of the hub.
   "Outer" refers to a location further from the longitudinal axis of the hub.
   "Slot" refers to an elongated through hole, e.g. cut into a flat plate or into the surface of a cylinder.
   "Chamfer" refers to a transitional edge between two faces of an object.
   "Slide" (or slider) refers to a rail, for example formed by a groove or a slot, which is adapted to guide a corresponding element according to a sliding movement along its longitudinal direction.

DETAILED DESCRIPTION

Figure 1:
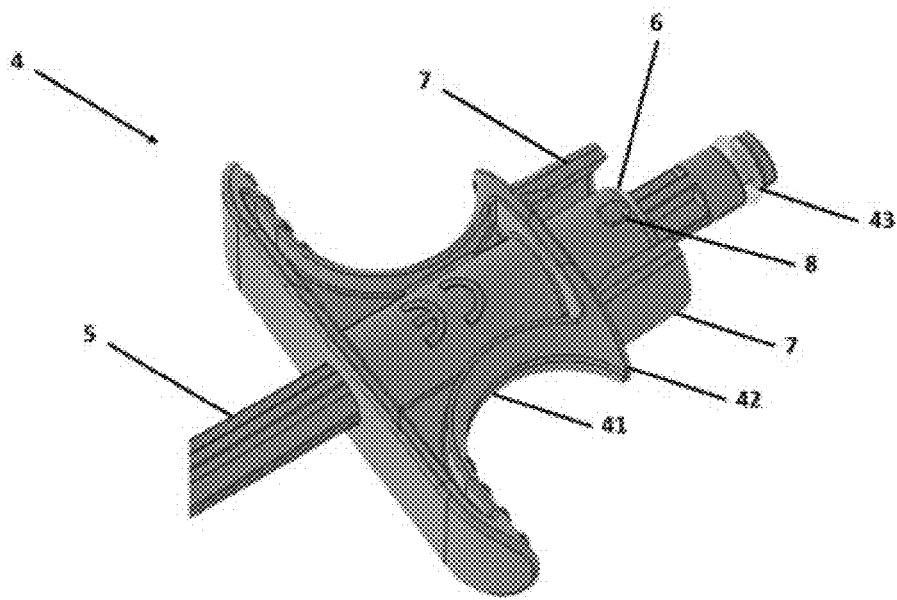
FIG. 1 is a perspective view of a syringe handle according to an embodiment of the invention.

The syringe according to the present invention comprises a handle and an injection body and ensures a locking function. In one embodiment, this locking function is preferentially ensured by a retaining function and a radial holding function.

The retaining function ensures the locking of the handle 4 and the injection syringe body 1 in translation and in rotation relative to each other.

In one embodiment, the retaining function is ensured by the cooperation of a female retaining means 26 of the injection syringe body 1 and a male means 8 of the handle 4. The following description describes different embodiments where the female retaining means 26 and the male retaining means 8 are configured in different manners.

In one embodiment, the radial holding function is ensured by the cooperation of the protective sheath 3 in the retracted position and at least one blocker 7. The following description describes different embodiments where the protective sheath 3 and the at least one blocker 7 are configured in different manners.

The radial holding function ensures the locking of the handle 4 and the injection syringe body 1 relative to each other and prevents the radial deformation of the injection syringe body and of the handle in the radial direction when a strain is applied during use. A radial deformation of the hub 2 of the syringe body may come to disengage the male means 8 from the female means 26.

The radial holding function and the retaining function cooperate with one another in such a way as to give a locking effect superior to what it would have been if only one of the two functions was provided alone.

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly it should be understood that where features mentioned in the appended claims are followed by reference signs, such signs are included solely for the purpose of enhancing the intelligibility of the claims and are in no way limiting on the scope of the claims.

The present invention relates to a syringe comprising a syringe handle 4 and a syringe body 1 comprising a safe locking system, quick and easy to mount, strongly reducing risks of pricking with the needle before and after use, and cost effective. The present invention further relates to a method of use of said syringe.

The syringe according to an aspect of the present invention relates to a syringe comprising an injection syringe body 1 and a syringe handle 4, configured to cooperate with one another in order to ensure a locking function between the injection syringe body 1 and the syringe handle 4. The injection syringe body 1 comprises a longitudinal hub 2 comprising at least one female retaining means 26 and a protective sheath 3 moveable along said longitudinal hub 2 and able to cover in a retracted position the at least one female retaining means 26. The syringe handle 4 comprises at least one male retaining means 8 intended to cooperate with the at least one female retaining means 26, ensuring a retaining function; said cooperation being named locking position.

In one embodiment, the syringe further comprises at least one blocker 7, said at least one blocker 7 ensuring a radial holding function when the retracted and the locking positions are both engaged. In one embodiment, the radial holding function is ensured by at least partially covering the protective sheath 3 with the at least one blocker 7.

The syringe according to another aspect of the present invention comprises at least one male retaining means 8 (also called male means) on the handle 4 configured to be inserted in at least one female retaining means 26 (also called female means) of a hub 2 of the syringe body 1. During use, male means 8 and female means 26 are covered by a protective sheath 3 in a retracted position. Furthermore, the syringe comprises at least one blocker 7. In the retracted position, the protective sheath 3 is radially blocked between the hub 2 of the syringe body and the at least one blocker 7. The at least one blocker 7 and the protective sheath 3 transform the portion of the hub 2 comprising the female means 26 into a rigid assembly without any risk of accidental disassembly. The disengagement of the male means 8 from the female means 26 by the deformation of the hub 2 is therefore avoided.

The method of use of the syringe according to an embodiment of the present invention is described below.

Figure 6:
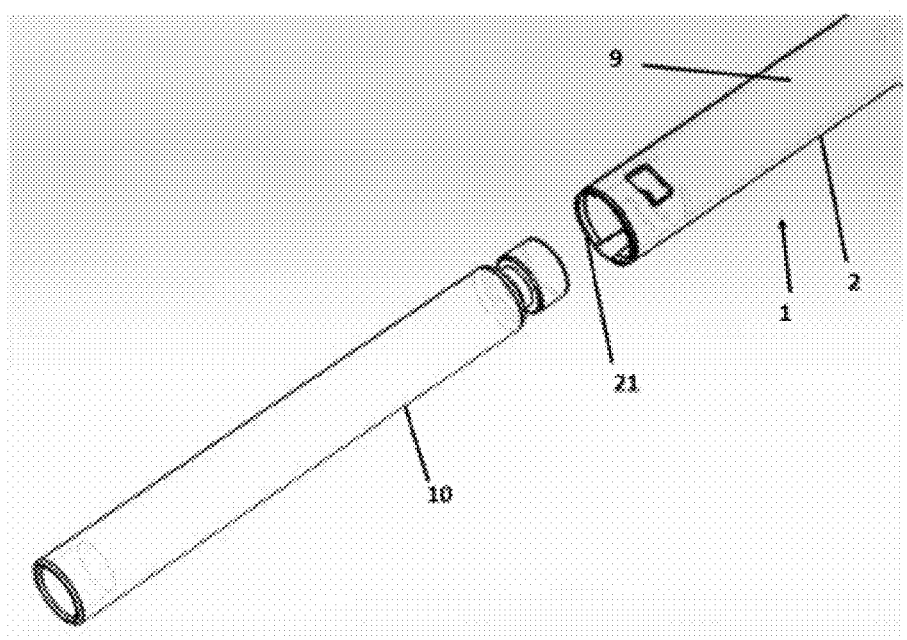
FIG. 6 is an exploded view of the longitudinal hub of the syringe body of FIG. 2A and a cartridge.

In a first step illustrated on FIG. 6, a cartridge 10 is inserted in the compartment 9 of the longitudinal hub 2 of the syringe body 1, more precisely in the first longitudinal open end 21 of the hub 2.

Figure 4A:
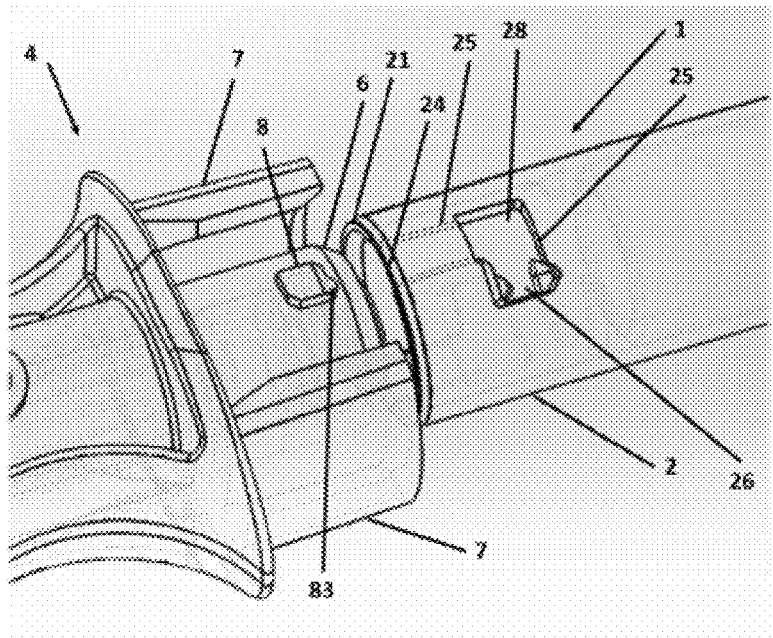
FIG. 4A is a perspective view of the syringe body and the syringe handle of FIGS. 1 and 2A before the insertion of the male means of the syringe handle in the female means of the syringe body.

In a second step, as shown in FIG. 4A, the first longitudinal end 21 of the syringe body 1 is presented in front of the sleeve 6 of the syringe handle 4 or the inlet 24 is presented in front of the male means 8.

In a third step, in a first embodiment, the male means 8 is inserted in the inlet 24 of the longitudinal hub 2 and moved along the longitudinal hub 2 until the male means 8 is positioned in the female means 26 in the locking position.

Figure 4B:
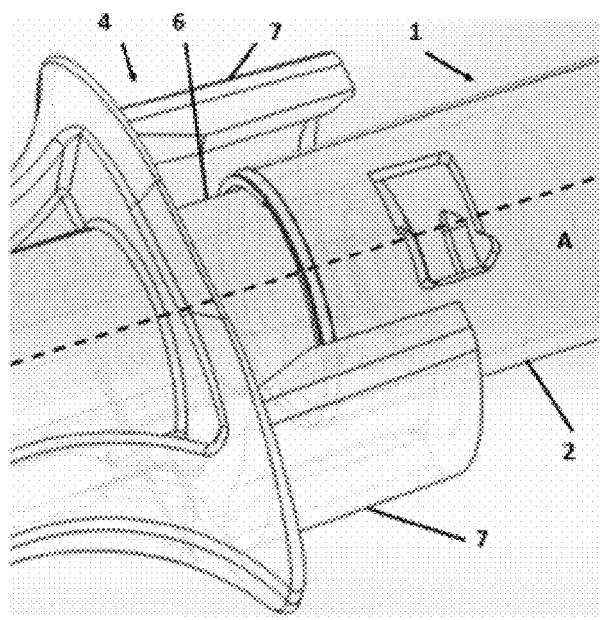
FIG. 4B is a perspective view of the syringe body and the syringe handle of FIGS. 1 and 2A at the beginning of the insertion of the male means of the syringe handle in the female means of the syringe body.
Figure 4C:
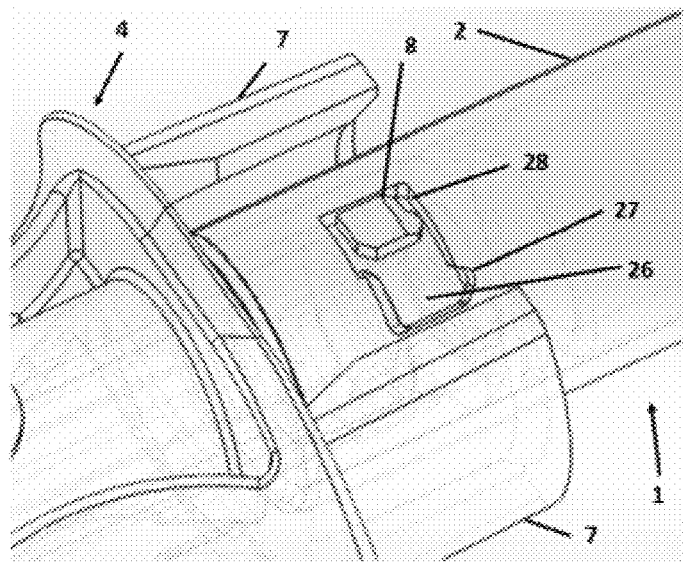
FIG. 4C is a perspective view of the syringe body and the syringe handle of FIGS. 1 and 2A when the male means is housed in an intermediate position in a first part of a slide.
Figure 4D:
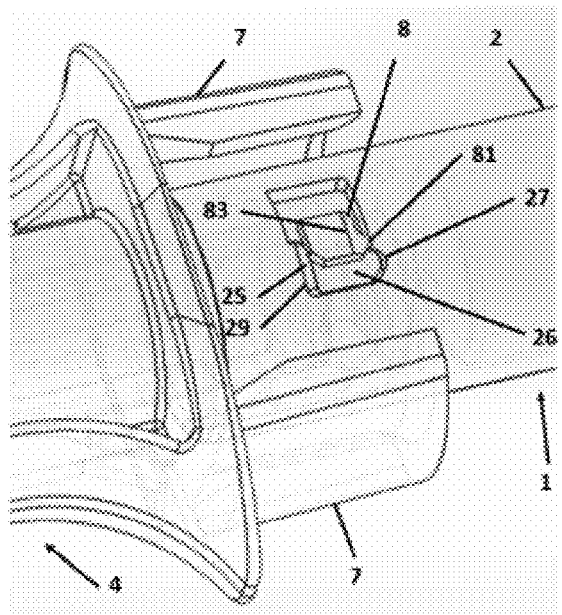
FIG. 4D is a perspective view of the syringe body and the syringe handle of FIGS. 1 and 2A when the male means is housed in a second part of the slide.
Figure 4E:
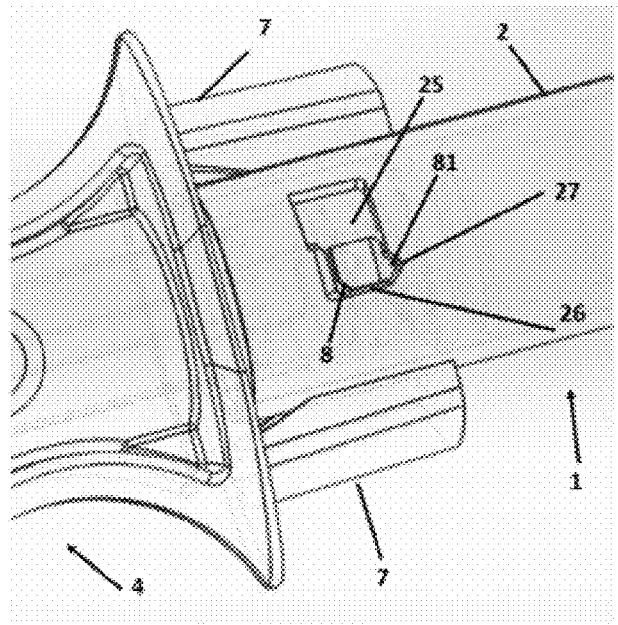
FIG. 4E is a perspective view of the syringe body and the syringe handle of FIGS. 1 and 2A when the male means is housed in the female means.

In a third step, in a second embodiment, as shown in FIG. 4B, the sleeve 6 of the syringe handle 4 is inserted into the longitudinal hub 2. Then, the handle 2 is moved along the longitudinal axis A of the longitudinal hub 2 until the male means 8 is lodged in the intermediate position 28 as shown in FIG. 4C. Finally, as illustrated in FIG. 4D, the syringe body 1 is moved in rotation with regard to the syringe handle by the technician and the male means 8 slides into the second part of the slide 25 to the female means 26 into the locking position. In said locking position, as shown in FIG. 4E, the return of the male means 8 into the slide 25 needs to deform the male means 8 and/or the hub 2, so that this return is not possible unless a minimum force is applied in reverse rotation by the technician.

Figure 5A:
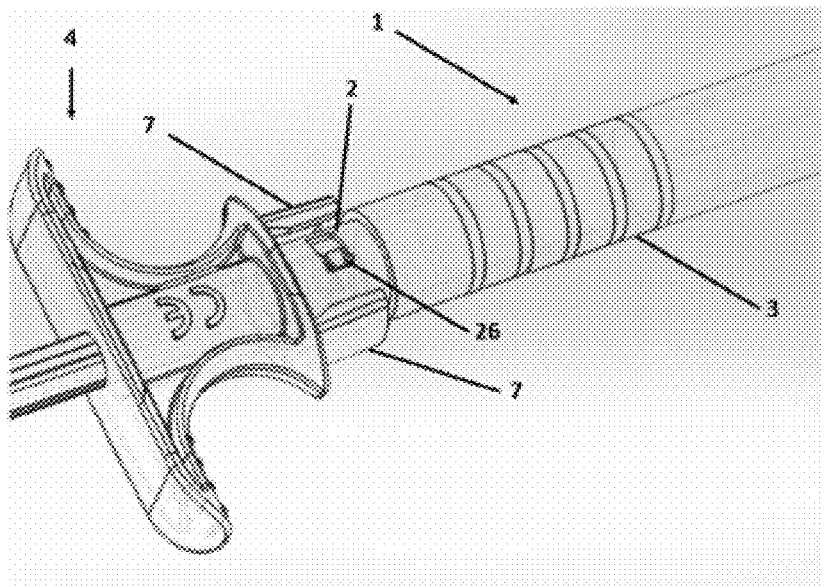
FIG. 5A is a perspective view of the syringe body and the syringe handle of FIGS. 1 and 2A before the protective sheath is retracted.
Figure 5B:
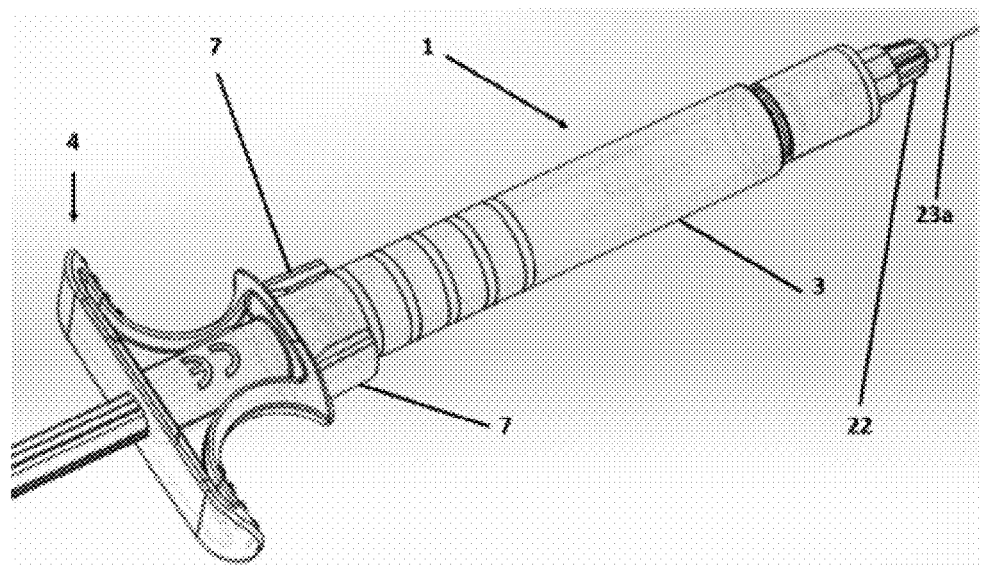
FIG. 5B is a perspective view of the syringe body and the syringe handle of FIGS. 1 and 2A after the protective sheath has been retracted to its retracted position.
Figure 5C:
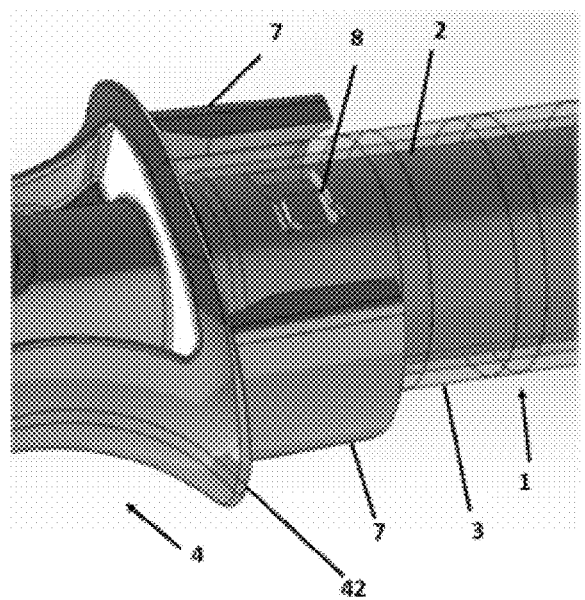
FIG. 5C is a perspective view at larger scale of the syringe body and the syringe handle of FIGS. 1 and 2A after the protective sheath has been retracted to its retracted position.

In a fourth step, the protective sheath 3 is moved along the longitudinal hub 2 to cover either the female means 26 or the first end of the longitudinal hub 21 in a retracted position as illustrated in FIG. 5A and FIG. 5B. As shown in FIG. 5C, the protective sheath 3 is radially inserted between the longitudinal hub 2 and the blockers 7. According to one embodiment, the movement of the protective sheath 3 along the longitudinal hub 2 from its extended position to its retracted position is limited by the plate 42 of the handle 4.

Said protective sheath 3, when the locking position and the retracted position are both engaged, is radially blocked between the longitudinal hub 2 and the at least one blocker 7 in order to avoid the disengagement of the male means 8 from the retaining means 26. The at least one blocker 7 and the protective sheath 3 transform the sleeve 6 and the portion of the hub comprising the female means 26 into an improved rigid assembly without any risk of accidental disassembly.

Optionally, the method comprises a fifth step consisting in penetrating a subject body and injecting the liquid of the cartridge by pushing the plunger 5.

After use, the technician may remove the protective sheath 3 from the blockers 7 in its extended position and can remove the handle 4 from the syringe body 1 without any risk of accidental pricking with the needle 23. According to one embodiment (not illustrated), the protective sheath 3 may be moved along the hub 2 from the extended position to an irreversible position in such a way that the extended position is located between said irreversible position and the retracted position. In said irreversible position, the protective sheath 3 is irreversibly positioned in a location where the external portion of the needle 23a is inside and/or protected by the protective sheath 3. In one embodiment, the protective sheath 3 cannot be moved along the hub 2 from the irreversible position to the extended position.

According to one embodiment, the cartridge is removed with the removal of the handle 4 because of the collar 43 causing a vacuum between said collar 43 and the cartridge 10 after the injection.

Figure 2A:
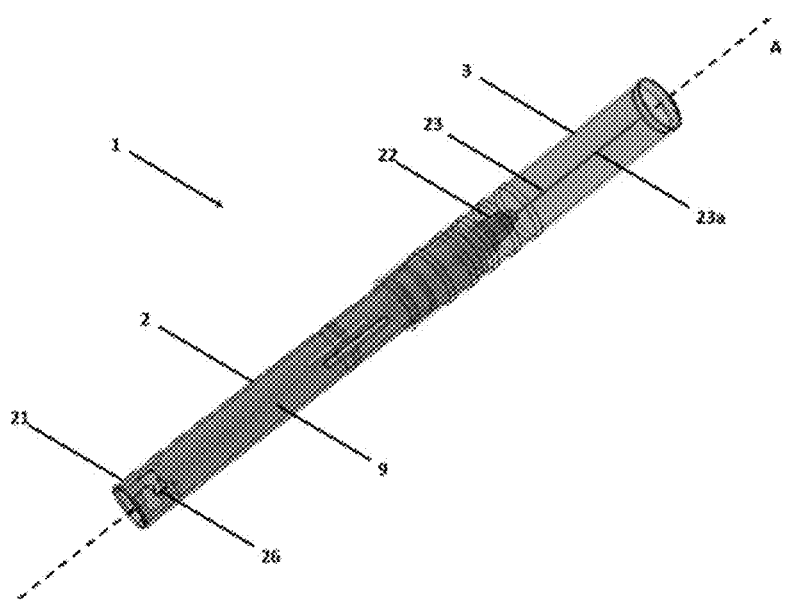
FIG. 2A is a perspective view of a syringe body according to an embodiment of the invention.
Figure 2B:
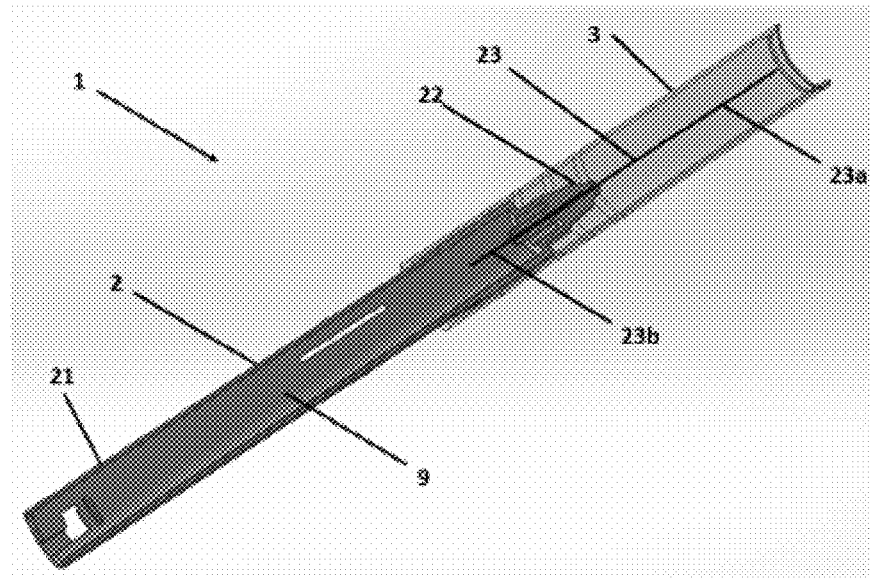
FIG. 2B is a perspective view of the syringe body of FIG. 2A, sectioned along a median longitudinal plane.

The syringe of the invention comprises two distinct elements: an injection syringe body shown in FIG. 2A and FIG. 2B and a syringe handle shown in FIG. 1. The injection syringe body 1 shown FIG. 2A comprises a longitudinal hub 2 and a protective sheath 3 adapted to slide along the syringe body in the longitudinal direction A of the hub.

The syringe handle 4 shown in FIG. 1 may comprise a sleeve 6 which can have the shape of a hollow cylinder. The syringe handle 4 may further comprise finger grip ribs 41 integral with the sleeve 6 and a plunger 5 adapted to slide inside the syringe handle 4 and in particular the sleeve 6.

In one embodiment, the plunger 5 comprises a rod of a diameter substantially smaller than the inside diameter of the sleeve 6. The plunger 5 may comprise an operating button which makes it possible to displace the plunger 5 inside the syringe handle 4 and the sleeve 6. According to one embodiment, the plunger 5 further comprises, at its end opposite from the operating button, a collar 43 having a diameter greater than the diameter of the rod of the plunger, the collar 43 ending at the open face of the sleeve 6. In said embodiment, the plunger 5 cannot be removed from the syringe handle 4.

According to one embodiment, the collar 43 has an outer diameter substantially equal to the inner diameter of the cartridge 10. In said embodiment, the expulsion of the liquid comprised in the cartridge 10, combined with the progression of the collar 43 inside the cartridge, creates a vacuum between the collar 43 and the cartridge 10. Said collar 43 enables the cartridge to be removed from the hub 2 with the removing of the syringe handle 4. Indeed, during the withdrawal of the plunger 5 from the longitudinal hub 2, the vacuum inside the cartridge 10 avoids the sliding of the collar 43 along the cartridge. Therefore, the cartridge 10 is removed from the hub 2 with the handle 4.

According to one embodiment, the sleeve 6 is able to be inserted into the longitudinal hub 2 of the syringe body 1.

In one embodiment, the sleeve 6 has a cylindrical form.

In one embodiment, the handle 4 is formed of a solid element and a plunger 5. According to one embodiment, the handle 4 is formed of a single molded part and a plunger 5. In one embodiment, the single molded part comprises the at least one blocker 7. In one embodiment, the single molded part comprises the finger grip ribs, the sleeve 6 and the at least one blocker 7.

The sleeve 6 comprises at least one male retaining means 8. Said male means 8 may be a projection, a protrusion or a pin. According to one embodiment, said male means 8 extends radially from the outer surface of the sleeve 6.

According to one embodiment, the male means 8 comprises a chamfer on its distal side in order to facilitate the penetration of the handle 4 into the longitudinal hub 2.

Furthermore, it should be understood that the male retaining means 8 and the female retaining means 26 may be switched. Indeed, in one embodiment (not illustrated), the hub 2 may comprise at least one male means protruding from its inner surface and the sleeve may comprise at least one female means configured to house the male means of the hub 2.

The syringe further comprises at least one blocker 7.

According to one embodiment, the syringe handle 4 further comprises at least one blocker 7. According to one embodiment, the at least one blocker 7 extends from the finger grip ribs. According to another embodiment, the syringe handle 4 comprises a plate 42 with a surface perpendicular to the longitudinal direction of the plunger 5. According to said embodiment, the plate 42 comprises a hollow in which is located the plunger 5.

In one embodiment, the sleeve 6 and the at least one blocker 7 extend from said plate 42 in a longitudinal direction parallel to the direction of the longitudinal axis of the plunger 5.

According to one embodiment, the at least one blocker 7 is a hollow cylinder having the same cylinder axis as the sleeve 6, and the inside diameter of the blocker 7 is higher than the outside diameter of the sleeve 6 or higher than the sum of the outside diameters of the sleeve 6 and the at least one male retaining means 8. According to one embodiment, the at least one blocker 7 is a gripper or a collet.

According to an alternative embodiment illustrated in FIG. 1, the syringe handle 4 comprises two blockers 7 and each blocker 7 is a portion of a hollow cylinder having the same cylinder axis as the sleeve 6, and the inside diameter of said hollow cylinder is higher than the outside diameter of the sleeve 6 or higher than the sum of the outside diameters of the sleeve 6 and the at least one male retaining means 8. In one embodiment, the syringe handle 4 comprises N blockers 7, with N being an integer greater than or equal to 2, and each blocker 7 is a portion of a hollow cylinder having the same cylinder axis as the sleeve 6, and the inside diameter of said hollow cylinder is higher than the outside diameter of the sleeve 6 or higher than the sum of the outside diameters of the sleeve 6 and the at least one male retaining means 8. In said embodiment, the N blockers are regularly positioned around the longitudinal axis of the plunger 5. By regularly positioned, it should be understood that the center point of each one of the N blockers is spaced from the center point of an adjacent blocker with an angle substantially equal to 360°/N.

According to one embodiment, the syringe handle comprises N blockers, with N being an integer greater than or equal to 2, said blockers being regularly positioned around the sleeve 6 of the handle, or around the protective sheath 3 of the syringe body when the handle is mounted with the syringe body.

According to another embodiment, the at least one blocker 7 is comprised in the syringe body or in the protective sheath.

According to one embodiment, the at least one blocker 7 is a collet or an annular ring around the protective sheath 3. In said embodiment, the at least one blocker is in metal or in plastic material.

According to one embodiment, the at least one blocker 7 is not the protective sheath 3 or is not comprised in the protective sheath 3.

According to one embodiment, the at least one blocker 7 comprises a threaded collar configured to be inserted around the protective sheath and to be screwed on the syringe handle 4 or on the syringe body 1. According to said embodiment, the handle 4 comprises a thread at its end aligned with the sleeve 6 but having an inner diameter greater than the outer diameter of the sleeve 6 and said thread is configured to cooperate with the threaded collar.

According to another embodiment, the syringe handle 4 comprises a thread and the protective sheath 3 comprises a thread configured to cooperate with the thread of the handle 4. The protective sheath 3 is screwed in the syringe handle 4, ensuring the rigidity of the protective sheath 3 and avoiding the deformation of the hub 2.

According to one embodiment, the longitudinal hub 2 has a hollow cylindrical form.

As illustrated in FIG. 2A and FIG. 2B, the longitudinal hub 2 comprises a first longitudinal end 21 and a second longitudinal end 22 opposite from the first longitudinal end 21 and further comprises a compartment 9 located between said first and second longitudinal ends. As illustrated in FIG. 6, the first longitudinal end 21 is open and the longitudinal hub 2 is configured to receive a cartridge 10 in said compartment 9. According to one embodiment, the longitudinal hub 2 is transparent in order to see the level of liquid remaining in the cartridge 10 during use.

The longitudinal hub 2 is provided at its second longitudinal end 22, as shown in FIG. 2B, with a sealed base carrying a needle or a cannula so as to define an external portion 23a extending outside said hub 2 and an internal portion 23b extending inside said hub 2.

The internal portion 23b of the needle 23 is configured to drill the cartridge 10 when said cartridge is in the compartment 9.

According to one embodiment, the longitudinal hub 2 has a cylindrical form and has an inside diameter corresponding to the outside diameter of the sleeve 6 of the syringe handle 4. The longitudinal hub 2 has, at its first end 21, an inside diameter adapted to house the sleeve 6 of the syringe handle 4.

According to one embodiment, the longitudinal hub 2 is made of polypropylene.

The longitudinal hub 2 comprises, at the vicinity of the first longitudinal end 21, at least one female means 26 configured to house the at least one male retaining means 8 of the handle 4. According to one embodiment, the female means 26 is a through hole, an aperture or an opening.

Figure 3:
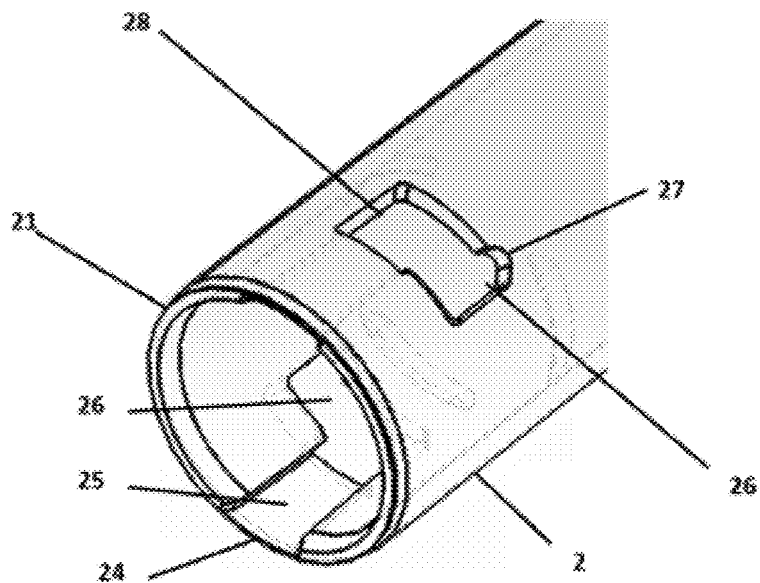
FIG. 3 is a view of a first longitudinal end of the longitudinal hub of the syringe body shown in FIG. 2A.

As illustrated in FIG. 3, the longitudinal hub 2 can comprise an inlet 24, and a slide 25 adapted to guide the male retaining means 8 of the handle 4 from the inlet 24 to the female means 26.

According to one embodiment, the slide 25 has an L-shape, the guiding of the male means 8 corresponding to a first translation in the longitudinal direction A of the hub 2 from the inlet 24 to an intermediate position 28 and a second translation in a transversal direction to the first translation direction from the intermediate position 28 to the female means 26. The slide 25 may be a groove cut into the inner surface of the hub 2. The slide 25 can have an inner diameter higher than the inner diameter of the hub 2. The slide 25 can also be a through slot or a blind slot cut into the inner surface of the hub 2.

In one embodiment illustrated in FIG. 3, the first portion of the slide 25 corresponds to a groove or a blind slot cut into the inner surface of the hub 2, the intermediate position is a through hole and the second portion of the slide 25 is a through slot.

In said embodiment, when the male means 8 is inserted into the inlet 24, as shown in FIG. 4A and FIG. 4B, the hub 2 and the male means 8 are out of shape until the male means 8 arrive in the opened intermediate position 28 as shown in FIG. 4C. The opened intermediate position 28 may be a through hole of a form adapted to fit with the male means 8.

In one embodiment, said male means 8 comprises a chamfer 83 on its side configured to be engaged in the inlet 24 (see FIG. 4A and FIG. 4D) in order to facilitate the deformation of said male means 8 or of the hub 2, and the engagement of the male means 8 in the slide 25. According to one embodiment, the side of the male means 8 opposite from the chamfer 83 presents a right angle in order to present a resistance force to the unlocking of the male means 8, i.e. to the extraction of the male means 8 out of the slide 25.

The second portion of the slide 25 is able to guide the male means 8 from the intermediate position 28 to the female retaining means 26. According to one embodiment, said second portion of the slide 25 is a slot or an elongated through hole.

According to one embodiment, the second portion of the slide 25 has a width narrower than the width of the female retaining means 26 and narrower than the length of the male means 8 according to the direction A in order to deform the male means 8 and/or the hub 2 during the sliding from the intermediate position 28 to the female retaining means 26 in the locking position. The dimensions of the female means 26 allow the hub 2 and/or the male means 8 to recover its original shape. Therefore, there is a resistance to make the male means 8 come back from the female retaining means 26 to the slide 25, which prevents the unintentional withdrawal of the male means 8 from the female retaining means 26. According to one preferred embodiment, the Young's modulus of the hub 2 is lower than the Young's modulus of the male means 8. In other terms, the hub 2 is deformed during the sliding and not the male means 8.

More generally, the Young's modulus of the part comprising the female means is lower than the Young's modulus of the male means or the part comprising the male means. In the case where the hub 2 comprises at least one male means protruding from its inner surface and the sleeve comprises at least one female means configured to house the male means of the hub 2, the Young's modulus of the male means of the hub 2 is higher than the Young's modulus of the sleeve 6.

According to one embodiment, the male means 8 comprise a lateral protrusion 81 (see FIG. 4D) in order to increase its length along the direction A, and the shape of the female means 26 is configured to fit with the male means 8 and its lateral protrusion 81. Said shape of the female means 26 can particularly comprise a cut 27 adapted to receive the protrusion 81 of the male means 8.

By "width of the second portion of the slide", it is meant here the dimension of the second portion of the slide along the direction A.

According to one embodiment, the second portion of the slide 25 further comprises a chamfer 29 (see FIG. 4D) on the opposite side from the cut 27 in order to facilitate the sliding of the male means 8 towards the female means 26. Indeed, in said second portion of the slide 25, the hub 2 is deformed when the male means 8 slides along said second portion of the slide 25. Therefore, the chamfer 29 makes it possible to reduce the surface of contact between the hub 2 and the male means 8 and thus to reduce the frictional force acting against the sliding. Furthermore, the shape of a chamfer for the male means in contact with the inner side of the hub 2 reduces the risk of disengagement of the handle 4 from the hub 2. Indeed, the hub 2 has to be more deformed to pass over the male means 8.

According to one embodiment, the longitudinal hub 2 comprises M female means 26, and the handle 4 comprises M male means 8 and each male means 8 is configured to be inserted in a female means 26. According to one embodiment, the M male means 8 are regularly positioned around the sleeve 6. By regularly positioned, it should be understood that each one of the M male means 8 is circumferentially spaced from the adjacent male means 8 with an angle substantially equal to 360°/M around the longitudinal axis of the plunger 5. In said embodiment, the M female means 26 are regularly positioned around the longitudinal hub 2. By regularly positioned, it should be understood that each one of the M female means 26 is circumferentially spaced from the adjacent female means 26 with an angle substantially equal to 360°/M around the longitudinal axis of the hub 2.

According to one embodiment, the insertion of the handle relative to the syringe body is not reversible. In said embodiment, the slide 25 comprises anti-return means at the junction with the female means 26. Said anti-return means unable the male means 8 to be slid from the female means 26 toward the slide 25. In other terms, said anti-return means make the displacement of the male means 8 from the female means 26 toward the slide 25 more difficult than its displacement from the slide 25 into the female means 26. Said anti-return means may be a rectangular step in the direction of the translation of the male means 8 out of the female means 26 toward the slide 25.

According to one embodiment, M is equal to 1, 2, 3, 4, 5, 6, 7, 8, 9 or more than 10. According to a preferred embodiment, M is equal to 2, and the 2 male means 8 are circumferentially spaced by an angle of 180° and the 2 female means 26 are circumferentially spaced by an angle of 180°. According to said embodiment, a first male means 8 can be inserted in any female means 26 interchangeably.

The protective sheath 3 is preferably made of a transparent material.

The protective sheath 3 has a cylindrical form or a form adapted to shield the external part of the needle 23 and the second end 22 of the longitudinal hub 2 with the sealed base carrying the needle 23.

The protective sheath 3 is tubular and has an inner diameter adapted to be able to slide externally along the longitudinal hub 2. According to one embodiment, the inner diameter of the protective sheath 3 is substantially equal to the outside diameter of the longitudinal hub 2 and is substantially equal or higher than the sum of the outside diameter of the sleeve 6 and the radial height of the male means 8 of the syringe handle 4.

The protective sheath 3 is moveable along the longitudinal hub 2 and along the longitudinal axis A of the longitudinal hub. According to one embodiment, the protective sheath 3 is moveable between at least two positions:
- an extended position where the external portion of the needle 23a is inside the protective sheath 3; and
- a retracted position where at least the end of the needle extends outside the protective sheath 3 and where said protective sheath covers the at least one female retaining means 26 or the first end 21 of the longitudinal hub 2.

According to one embodiment, the protective sheath 3 is moveable along the longitudinal hub 2 and/or along the longitudinal axis A of the longitudinal hub from the extended position to an irreversible position, where the extended position is located between the retracted position and the irreversible position. In said irreversible position, the protective sheath 3 is irreversibly positioned in a location where the external portion of the needle 23a is inside and/or protected by the protective sheath 3.

According to one embodiment, the hub 2 comprises, in the vicinity of its second longitudinal end 22, at least one anti-return means configured to cooperate with at least one anti-return means of the protective sheath 3, so that once the anti-return means of the protective sheath 3 is between the anti-return means of the hub 2 and the second longitudinal end 22, said anti-return means of the protective sheath 3 cannot be moved between the anti-return means of the hub 2 and the first longitudinal end 21 of the hub 2.

The advantage of this irreversible position is that the operator does not have to put a protective case on the tip of the needle 23 after use, the operator only has to put the protective sheath 3 in the irreversible position to protect the tip of the needle 23.

According to one embodiment, the irreversible position and the retracted position are extreme positions.

The protective sheath 3 has an outside diameter configured to be in contact with the at least one blocker 7 when the protective sheath is in the retracted position and the syringe handle 4 is mounted on the syringe body 1.

According to one embodiment, the syringe according to the present invention may comprise 2, 3, or at least 4 male means 8 and the same number of female means 26 and optionally the same number of inlets 24 and slides 25 according to the above description.

The present invention further relates to a syringe handle 4 adapted to cooperate with an injection syringe body 1 of the present invention, said syringe handle 4 comprising:
- at least one male retaining means 8 intended to cooperate with the at least one female retaining means 26 of the injection syringe body 1 ensuring a retaining function, said cooperation being named locking position; and
- at least one blocker 7 adapted to cooperate with a protective sheath 3 of the injection syringe body 1 in a predefined position, the at least one blocker ensuring a radial holding function when the predefined position of the protective sheath 3 and the locking position are both engaged.

The present invention further relates to an injection syringe body 1 adapted to cooperate with a syringe handle 4 according to the present invention and comprising:

a longitudinal hub 2 comprising at least one female retaining means 26 configured to maintain longitudinally a male retaining means 8;

a protective sheath 3 moveable along said longitudinal hub 2 and able to cover in a retracted position the at least one female retaining means 26, wherein the cooperation between the injection syringe body 1 and a syringe handle 4 is locked when the retracted position is activated.

The present invention further relates to a kit comprising an injection syringe body 1 according to the present invention, a cartridge 10 and a sterilized packaging bag of said injection syringe body 1 and said cartridge 10.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A syringe comprising an injection syringe body and a syringe handle, configured to cooperate with one another in order to ensure a locking function between the injection syringe body and the syringe handle;

the injection syringe body comprising:
a longitudinal hub comprising at least one female or male retaining means, and
a protective sheath moveable along said longitudinal hub and able to cover in a retracted position the at least one retaining means of the longitudinal hub;

the syringe handle comprising:
at least one male or female retaining means intended to cooperate with the at least one female or male retaining means of the longitudinal hub, ensuring a retaining function, said cooperation being named locking position, wherein the syringe further comprises at least one blocker, said at least one blocker ensuring a radial holding function when the retracted and the locking positions are both engaged, wherein each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide.

2. The syringe according to claim 1, wherein the anti-return means comprise a width of the slide which is narrower than the width of the female retaining means and narrower than the length of the male retaining means according to a longitudinal direction of the longitudinal hub.

3. The syringe according to claim 1, wherein the anti-return means comprise a step in the direction of the translation of the male retaining means out of the female means toward the slide.

4. The syringe-e according to claim 1, wherein the slide comprises at least two portions, forming an angle at the boundary between the two portions.

5. The syringe according to claim 1, wherein the slide has an L-shape.

6. The syringe according to claim 4, wherein the slide comprises at least one through slot between the boundary between the two portions of the slide and the female retaining means.

7. The syringe according to claim 1, wherein the Young's modulus of the part comprising the female retaining means is lower than the Young's modulus of the male retaining means.

8. The syringe according to claim 1, comprising at least two blockers and wherein, when the retracted and the locking positions are both engaged, the at least two blockers are regularly positioned around the protective sheath, ensuring the radial holding function by at least partially covering the protective sheath.

9. The syringe according to claim 1, wherein the syringe handle comprises said at least one blocker.

10. The syringe according to claim 1, wherein the at least one retaining means of the longitudinal hub is located in the vicinity of a first longitudinal end of the hub and the injection syringe body further comprises a needle fitted with a second end of said hub opposite from said first end, said needle comprising an external portion extending outside said hub.

11. The syringe according to claim 10, wherein the protective sheath is moveable along said hub between at least two positions:
an extended position, where the external portion of the needle is inside the protection sheath; and
the retracted position where at least a part of the external portion of the needle is extended outside the protective sheath and said protective sheath covers the at least one retaining means.

12. The syringe according to claim 10, wherein the longitudinal hub further comprises a compartment between the first end and the second end configured to receive a cartridge.

13. The syringe according to claim 1, wherein the inner diameter of the protective sheath is equal to the outer diameter of the longitudinal hub.

14. The syringe according to claim 1, wherein the at least one blocker is curved and the radius of curvature of the inner surface of the at least one blocker is equal to the radius of curvature of the outer surface of the protective sheath.

15. The syringe according to claim 5, wherein the slide comprises at least one through slot between the boundary between the two portions of the slide and the female retaining means.

16. A syringe handle adapted to cooperate with an injection syringe body, said injection syringe body comprising at least one female or male retaining means and at least one protective sheath moveable along a longitudinal hub of the injection syringe body, said syringe handle comprising:
at least one male or female retaining means intended to cooperate with at least one female or male retaining means of the injection syringe body, ensuring a retaining function, said cooperation being named locking position; and
at least one blocker adapted to cooperate with a protective sheath of the injection syringe body in a predefined position, the at least one blocker ensuring a radial holding function when the predefined position of the protective sheath and the locking position are both engaged, wherein each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide.

17. An injection syringe body adapted to cooperate with a syringe handle comprising at least one male or female retaining means, said injection syringe body comprising:
a longitudinal hub comprising at least one female or male retaining means configured to maintain longitudinally a male or female retaining means of a syringe handle;

a protective sheath moveable along said longitudinal hub and able to cover in a retracted position the at least one female or male retaining means of the longitudinal hub, wherein the cooperation between the injection syringe body and a syringe handle is locked when the retracted position is activated, wherein each female retaining means of the longitudinal hub and/or the handle is connected to a slide for guiding a male retaining means from an inlet into the female retaining means, said slide comprising anti-return means forming a resistance to a displacement of the male retaining means from the female retaining means to the slide.

* * * * *